United States Patent
Iovanni et al.

(10) Patent No.: US 9,304,518 B2
(45) Date of Patent: Apr. 5, 2016

(54) MODULAR AUTOMATED CHROMATOGRAPHY SYSTEM

(75) Inventors: Robert Iovanni, Vallejo, CA (US); Alec Gordon, San Francisco, CA (US); Bob Avarbock, Benicia, CA (US); Wayne Bland, Martinez, CA (US); Glenn Price, Martinez, CA (US); Ken Baker, Martinez, CA (US); Farah Mavandadi, San Mateo, CA (US); Christof Schultz, Orinda, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 589 days.

(21) Appl. No.: 13/591,461

(22) Filed: Aug. 22, 2012

(65) Prior Publication Data
US 2013/0218352 A1 Aug. 22, 2013

Related U.S. Application Data

(60) Provisional application No. 61/526,959, filed on Aug. 24, 2011.

(51) Int. Cl.
*B01D 15/14* (2006.01)
*B01D 15/18* (2006.01)
(Continued)

(52) U.S. Cl.
CPC .............. *G05D 7/0617* (2013.01); *B01D 15/18* (2013.01); *G01N 30/465* (2013.01);
(Continued)

(58) Field of Classification Search
CPC .... B01D 15/10; B01D 15/14; B01D 15/1864; B01D 15/1871; B01D 15/1878; B01D 15/1885; G01N 30/02; G01N 30/16; G01N 30/24; G01N 30/46; G01N 30/461; G01N 30/463; G01N 30/465; G01N 30/466; G01N 30/467; G01N 30/468; G01N 2030/8881; G01N 2035/00326; G01N 2030/8804; G01N 30/88; G05D 7/06; G05D 7/0617
USPC ........... 73/61.56, 61.57; 210/143, 198.2, 656; 422/70, 509, 527, 566, 567; 700/273, 700/282
See application file for complete search history.

(56) References Cited

U.S. PATENT DOCUMENTS 5,580,523 A * 12/1996 Bard ................................ 422/50
5,588,109 A * 12/1996 Dickinson et al. ............ 715/740

(Continued)

FOREIGN PATENT DOCUMENTS

WO 2010/116389 A1 10/2010
WO 2010/144037 A1 12/2010

OTHER PUBLICATIONS

International Search Report and Written Opinion for PCT/US12/52001, mailed on Nov. 6, 2012, 16 pages.

(Continued)

*Primary Examiner* — Joseph Drodge
(74) *Attorney, Agent, or Firm* — Kilpatrick Townsend And Stockton LLP (57) ABSTRACT

Valves, pumps, detectors, sample loops, fraction collectors and the like are individually incorporated into modules that are mountable in interchangeable manner at individual mounting sites on a base unit which also supports one or more chromatography columns. Each module includes fluid connections to other modules and a microcontroller joining the module to a computed and monitor through an electronic connector at each mounting site. The fluid connections between the modules and the column(s) are removed from the electronic connections and accessible to the user. A software platform recognizes the modules and their locations, coordinates fluid connections between the modules, and provides a variety of control, monitoring, data generating and data processing functions to generate chromatographic data.

27 Claims, 6 Drawing Sheets

(51) Int. Cl.
  *G01N 30/16* (2006.01)
  *G01N 30/46* (2006.01)
  *G05D 7/06* (2006.01)
  *G01N 30/88* (2006.01)
  *G01N 35/00* (2006.01)

(52) U.S. Cl.
  CPC ............ *G01N 30/468* (2013.01); *G01N 30/88* (2013.01); *G01N 2030/8804* (2013.01); *G01N 2030/8881* (2013.01); *G01N 2035/00326* (2013.01)

(56) References Cited

U.S. PATENT DOCUMENTS

| | | | |
|---|---|---|---|
| 5,746,976 | A | 5/1998 | Yamada et al. |
| 5,766,460 | A * | 6/1998 | Bergstrom ............ B01D 15/08 210/198.2 |
| 5,801,699 | A * | 9/1998 | Hocker et al. ................. 715/837 |
| 6,260,407 | B1 * | 7/2001 | Petro et al. ................... 73/61.52 |
| 6,530,260 | B1 | 3/2003 | Mustacich et al. |
| 6,532,978 | B1 | 3/2003 | Muller-Kuhrt |
| 6,656,430 | B2 * | 12/2003 | Sheppard et al. ............... 422/63 |
| 7,566,395 | B2 | 7/2009 | Lundblad et al. |
| 7,770,125 | B1 * | 8/2010 | Young et al. .................. 715/764 |
| 8,701,012 | B1 * | 4/2014 | Selman et al. ................. 715/738 |
| 2002/0014106 | A1 * | 2/2002 | Srinivasan ........... B01J 19/0046 73/23.42 |
| 2002/0199094 | A1 | 12/2002 | Strand et al. |
| 2003/0001898 | A1 * | 1/2003 | Bernhardson ................. 345/786 |
| 2004/0143402 | A1 * | 7/2004 | Colinge et al. ................... 702/19 |
| 2006/0004330 | A1 | 1/2006 | Carlisle et al. |
| 2006/0027490 | A1 * | 2/2006 | DeMarco ................... 210/198.2 |
| 2008/0135115 | A1 | 6/2008 | Johansson et al. |
| 2008/0233018 | A1 * | 9/2008 | van Dam et al. .............. 422/159 |
| 2008/0233653 | A1 * | 9/2008 | Hess et al. ...................... 436/43 |
| 2009/0039024 | A1 | 2/2009 | Jenkins et al. |
| 2009/0150087 | A1 * | 6/2009 | Steinecker ...................... 702/24 |
| 2009/0305392 | A1 * | 12/2009 | Alfredsson et al. ........ 435/286.1 |
| 2009/0321338 | A1 * | 12/2009 | Natarajan .................. 210/198.3 |
| 2010/0032603 | A1 | 2/2010 | Wilen |
| 2010/0032604 | A1 | 2/2010 | Wilen |
| 2010/0044288 | A1 | 2/2010 | Kitagawa et al. |
| 2010/0058841 | A1 | 3/2010 | Wilen |
| 2010/0101411 | A1 * | 4/2010 | Tipler ............................... 95/86 |
| 2010/0113288 | A1 * | 5/2010 | Adey et al. ....................... 506/7 |
| 2010/0127200 | A1 | 5/2010 | Kallback et al. |
| 2011/0029256 | A1 * | 2/2011 | Frank .............................. 702/25 |
| 2011/0116973 | A1 | 5/2011 | Choikhet |
| 2011/0120951 | A1 * | 5/2011 | Hampton et al. ............. 210/657 |
| 2011/0240899 | A1 | 10/2011 | Wilen |
| 2011/0258566 | A1 * | 10/2011 | Oustiougov et al. .......... 715/766 |
| 2012/0005604 | A1 * | 1/2012 | Wirch et al. ................... 715/765 |

OTHER PUBLICATIONS

Extended European Search Report from EP Appl. No. 12825026.3, mailed Mar. 7, 2015.

* cited by examiner

MODULAR AUTOMATED CHROMATOGRAPHY SYSTEM

CROSS-REFERENCE TO RELATED APPLICATION

This application claims the benefit of U.S. Provisional Patent Application No. 61/526,959, filed Aug. 24, 2011, the contents of which are incorporated herein by reference in their entirety.

BACKGROUND OF THE INVENTION

1. Field of the Invention

This invention resides in the field of automated chromatography systems.

2. Description of the Prior Art

The extraction and purification of proteins, peptides, nucleic acids, monoclonal antibodies, and other species of interest from biological samples, as well as from reaction mixtures and fluid media in general, are critical procedures for research laboratories, diagnostic laboratories, drug manufacturing operations, and any number of settings and locations in the biotechnology industry. These procedures have reached such a high level of sophistication that virtually any biological species can be obtained in a highly purified form. Each species has its own special needs however in terms of such factors as sample preparation, the type and composition of separation media, and the conditions under which separation is performed. To meet all of its purification needs, therefore, the typical laboratory must accommodate a variety of components, protocols, and materials. Flexibility and adaptability are needed but are often obtained at the expense of consistency and accuracy, and the ability to accommodate a variety of protocols and to do so with the requisite accuracy often entails high costs in equipment, labor, and training.

SUMMARY OF THE INVENTION

The present invention addresses this need in a system that is easy and inexpensive to operate and that is highly adaptable to the separation and purification of different species and the protocols needed for each species. The system is easily and quickly assembled, reconfigured, substituted, and expanded, and, when the system is in use, its operation is readily monitored, controlled, and maintained. Even with complex flow schemes, the fluidics lines of the system are accessible to the user and managed in a neat and logical manner, while the electrical connections are confined to locations apart from those of the fluidics lines and are hidden from view. Most, if not all, of the electrical connections can be achieved through sockets, although certain embodiments of the invention include cables for some or all of the electrical connections.

The system is modular in construction, including a variety of modules, each module containing a fluid manipulation component and a microcontroller, and in certain embodiments of the invention additional features for control, status monitoring, and operation of the component in the module. Central to the system is a mounting frame or base unit with individual and interchangeable mounting sites for the various modules and a signal connector, such as for example an electronic connector, in each mounting site. Each of the signal connectors communicates with a common software platform, and the signal connectors couple interchangeably with the microcontrollers upon contact and communicate with the microcontrollers to which they are coupled. The connectors can also deliver electrical power to the modules, eliminating the need for separate wires or cables. Once the modules are mounted to the mounting frame in any of a variety of arrangements at the selection of the user, various functions are performed by the software, including recognition of the fluid manipulation components and their locations on the mounting frame by electronic signals transmitted through the couplings, and coordination of the components into a flow scheme. Fluid connections are made directly between the mounted components by the user, and in many embodiments this is done according to instructions provided by a graphical user interface powered by the software. Visual cues can also be provided by the modules near the locations where fluid connections are to be made. The mounting frame thus provides a central command and signal processing function to operate the full assemblage of components, using signal connections to and from each module, while all fluid connections are made between the components themselves, spatially separated from the electrical and signal connections and not part of the frame itself.

In certain embodiments of the invention, the mounting frame also provides one or more mounting stations in addition to the module mounting sites, these additional stations providing sites for mounting chromatographic separation units such as columns and cartridges, as well as fluid reservoirs or other media-retaining units that may not be appropriately sized for the module mounting sites. Units mounted at these additional locations can be fluidically joined to the components that are part of one or more of the various modules. The stations at which these columns, cartridges or other additional units are mounted can also be equipped with sensors or electronic connectors for transmitting information between the units so mounted and the mounting frame software.

In certain embodiments of the invention, two or more mounting frames, each fully equipped with a set of modules and each forming a self-contained purification system and fluidics scheme, can serve as separate and independent workstations, with all such workstations connected to a common central processing unit and database management system.

Systems in accordance with the present invention can thus accommodate a wide range of separation media and fluid transfer components. The features and embodiments cited above, together with other features and embodiments of the invention, are described in detail below.

DETAILED DESCRIPTION OF THE INVENTION AND SELECTED EMBODIMENTS

Modules. The term "module" is used herein to denote one or more functional devices affixed to a plate, an enclosure, or a supporting structure in general that is of standardized shape and size, the standardization enabling the module to be received, inserted, or otherwise affixed to any of a plurality of sites on the mounting frame. The standardized construction of the modules also enables each module upon mounting to the frame to engage the central user interface and software through couplings that join the microcontrollers on the modules to the signal connectors in the frame. As noted above, each module contains at least one fluid manipulation component and at least one microcontroller, plus any other devices necessary for the operation of the fluid manipulation device, and mounting features that mate with complementary mounting features at sites on the mounting frame. In a valve module, for example, the fluid manipulation device will be a valve, and the module can also contain a motor or actuating device as needed to rotate or actuate the valve. Actuating or operational supporting devices for any other type of fluid manipulation component will be readily apparent to those skilled in chromatographic and fluid flow equipment. The mounting structures on the modules can be tabs, pegs, hooks, latches, flanges, or anything for which a complementary structure can be built into the frame such as a slot, a shelf, a groove, a contoured recess or opening, for a secure mounting.

Fluid manipulation components. The term "fluid manipulation component" is used herein to denote components through which fluid passes or components that direct the flow of fluid in a particular direction. Examples of functions that a fluid manipulation component might perform are: driving the flow of fluids, combining or dividing fluids, detecting fluids, analyzing fluids, and measuring fluids. Examples of fluid manipulation components are: valves, pumps, mixers, sample loops, detectors, and fraction collectors. The valves can be simple shut-off valves or multi-port valves including rotary valves; the pumps can be rotary pumps, peristaltic pumps, syringe-type pumps, gradient pumps, or other laboratory-scale pumps; the detectors can be single-wavelength UV detectors, UV-Vis detectors, conductivity detectors, pH detectors, refractive index detectors, fluorescence detectors, pressure detectors, temperature detectors, or air or gas sensors; and the mixers can include proportioning mixers, either constant or variable.

Microcontrollers. The microcontrollers that are embedded in each module can be conventional integrated circuits, each containing a processor core, a memory, and programmable input/output peripherals. The microcontroller encodes machine-readable data which can include the identity of the component contained in the module, for example, as well as operational characteristics and features of the component, and real-time operational status of the component. The data can thus be readable by the system to inform the software of the identity of the component, i.e., whether the component is a valve, a detector, or any of the other types of components listed above, whether the component is currently operating or on standby, the flow rate through the component if operating, temperature, pressure, position the case of a valve, and the like. The microcontroller can also transmit operational signals to the component in response to commands received from a computer that is either incorporated into or external to the mounting frame. In certain embodiments, the microcontroller also detects malfunctions of the fluid manipulation component, such as those indicated by a rising pressure, a rising temperature, or a failure to respond to a command. The microcontroller in these embodiments will then emit an alarm signal alerting the user or the system software of the malfunction. An alarm indicator can be included on an exposed surface of the module, and the alarm can be a visually observable change in the indicator, such as a light turning on. Microcontrollers in certain embodiments of the invention can contain or be coupled to radio-frequency identification ("RFID") tags that can be updated by the user or by the module itself to contain information regarding current status of the fluid manipulation component or accumulated data pertaining to its use.

Component status indicators. An optional feature for inclusion in a module is a display that indicates the operational status of the component contained in the module on a real time basis. The status information, which will be readable by the user and specific to the component, can indicate for example the position of a valve, the flow rate through a valve or a pump, the direction of a pump, the action of a detector in detecting species in solution or a change in condition, the pressure in a pump, and any such indicator from which the user can visually detect whether the component is operating normally or is experiencing malfunction. The status indicator can be any device that transmits a visual or otherwise detectable signal, that can be mounted to the exterior surface of the module, and that can display the status information in a user-readable form, such as a numeric or graphical form or simply by an indicator light. A liquid crystal display (LCD) is one example of such an indicator; other examples will be readily apparent to those of skill in the art.

Mounting Sites and mounting frame; modular and interchangeable character of modules. The mounting sites are thus complementary to the modules both in their mounting features and in the locations of the signal connectors in the mounting sites relative to the microcontrollers on the modules, such that any module can be mounted to any of different mounting sites. Examples of mounting sites are slots, cavities, indentations, brackets, bays, or any such structure that will support a module in a secure and fixed position to minimize or avoid the possibility of disengagement through jostling of, or inadvertent impacts to, the module or the mounting frame. A simple example is a mounting site designed for a module to be slid into position at the site. The mounting frame is generally a chassis or structure with mounting members at designated sites on the structure that serve as mounting sites, and can thus be a support rack with cavities, bays, or open spaces in general for insertion of the modules. Most conveniently, the mounting sites can be spatially arranged in a regular geometric pattern, such as rows, columns, or a two-dimensional grid of rows and columns. Certain modules can be designed to occupy two or more adjacent mounting sites, and thus for example the mounting frame can include bays with widths or heights that are multiples of those of other bays, such as to accommodate double-width and triple-width, or double-height and triple-height, modules in addition to modules that occupy single mounting sites. Such doubling or tripling can be achieved for example by constructing the mounting sites as bays that are separated by vertical or horizontal barriers that are removable to combine adjacent bays. In still further embodiments, the mounting frame can be constructed to allow expansion of its module capacity by the addition of further rows or columns of mounting sites that can be supplied as accessories to the mounting frame.

In certain embodiments of the invention in which the mounting sites are arranged in two or more rows, the rows are fixed relative to each other, with all mounting sites accessible from one side of the mounting frame. The components of the various modules in these embodiments will be substantially coplanar, i.e., in substantially a common vertical plane at the front of the mounting frame. In many cases, this will improve the ease of making fluidic connections between the components mounted to the frame through their modules. In other embodiments of the invention where the mounting sites are arranged in two or more rows, one or more of the upper rows are secured to the underlying rows in a swiveling or rotatable manner, allowing the upper row(s) to be rotated relative to the row(s) beneath, the axis of rotation being vertical axis and passing through the center of the frame. In certain flow schemes, this rotation can improve access to or from certain fluid manipulation components. Fluid reservoirs that are placed to one side of the mounting frame, for example, can be connected to valves, pumps, meters, and other components on the frame with shorter lengths of tubing, and a column mounted to one side of the frame can likewise benefit from shorter tubing connections to pumps, detectors, or the like mounted to one of the mounting sites. Shorter tubing lengths will minimize the mixing of species, fractions, and liquids in general between the mounted components, where such mixing might lessen the resolution between bands of analytes, lower the slopes of pH or salt gradients, or lessen the sharpness of a stepwise change in fluid composition when such a change is part of a protocol. In some cases, the rotation capability may require longer tubing lines connecting some of the components. Certain modules, for example, may have fluid manipulation components that protrude from the frame when the modules are mounted in one of the mounting bays and extend above, below, or to one side of the projected dimensions of a single bay, hindering the placement of modules with a similarly protruding components in neighboring bays. Rotation of one row of bays in these cases will allow the modules to be mounted without interfering with each other. One arrangement that will accommodate these and other needs is a mounting frame with four rows of mounting bays, the two uppermost rows being rotatable relative to the two lower non-rotatable rows, and independently of each other. For safety, the rotatable rows in certain embodiments can be automatically locked in position when electrical power is supplied to the mounting frame and released for rotation only when the power is off.

Column rack. The fluid manipulation component on one or more modules can be a chromatographic column. Chromatographic columns can also (or alternatively) be positioned and/or supported separately from the mounting frame with appropriate fluidic connections to the components in the modules. A further alternative is to mount such columns to the mounting frame at sites separate from the module mounting sites, since the columns will typically be able to function without being interchangeable with the fluid manipulation components in a flow scheme. The column mounting sites can be included in a column rack at locations on the mounting frame that are apart from the module mounting sites and that do not interfere with fluidic or operator access to the modules and their components. Thus, with the module mounting sites on a front face of the mounting frame and the electrical connections at the back face of the mounting frame, the column rack can be on one of the side faces and yet accessible to the modules on the front face for fluid tubing connections to the modules. The rack can be designed to accommodate either a single column or two or more such columns, and in the latter case one or more of the rack positions can be left vacant occupied at the option of the user, mounting only the number of columns that are needed for a selected flow scheme. Information pertaining to the columns on the rack can be incorporated into the data used and displayed in the system by including identifier tags on the columns that are readable by the system software, and in certain cases, that are capable of having information added to them by the user through the system software. Examples of such tags are radio-frequency identification ("RFID") tags; other examples will be readily apparent to those of skill in the art. The information contained in a single tag can include the type of column, such as for example affinity, ion-exchange, hydrophobic interaction, gel filtration, or isoelectric focusing. The information can also include the column volume, the separation medium in the column, and the history of use of the column, such as the number of separations performed in the medium, the pressure the column experienced when last used, the last date at which the column was cleaned in place and the conditions using in the cleaning, and the results of the last column performance test. To read and utilize these tags, the rack can contain sensors appropriate to the particular tags, and the information transmitted by the sensors to the system software can include the location on the rack at which the column has been mounted in addition to all of the other information contained in the tag.

Software platform. Embedded in the mounting frame in certain embodiments of this invention is a server containing a suite of firmware, i.e., fixed programs or data structure to support the communication with and operation of the microcontrollers, and one or more libraries of operating programs for individual fluid manipulation devices or for pre-established fluidics schemes, or both. The mounting frame in many embodiments is also equipped with a touch screen monitor, preferably one measuring ten inches (25.4 cm) or greater. The touch screen monitor can serve as a GUI (graphical user interface) and can be equipped with USB (universal serial bus) ports for data import or export, ports for a keyboard and mouse, and jacks for LAN (local area network) or Ethernet cables. Alternatively, the mounting frame can include a mounting site for a tablet PC such as an Apple iPad or any such device that has an installed application that allows the device to function as the touch screen. Alternatively to, or in conjunction with, the touch screen monitor or tablet PC, a standard desktop personal computer with a conventional operating system such as Microsoft WINDOWS can be used for operation and control. When both a touch screen monitor mounted directly to the mounting frame and a desktop computer external to the mounting frame are used, the two can be connected through an LAN, an Ethernet, or any other standard communication protocol, either wired or wireless.

Certain embodiments of the invention also contain programmable software embedded in either the mounting frame or the desktop computer. This software can be programmed to interrogate each microcontroller in the various modules for the machine-readable data encoded in the microcontroller, and to do so immediately upon the mounting of each module to the mounting frame. The microcontroller can respond to the interrogation by sending a signal back to the system software, and the software can correlate the signal with an embedded library to determine the type and/or identity of the component in the module. The response from the microcontroller can also contain instructions for the commands that the module requires for operation. The software will then record the identity and location of the component and display this information on the GUI in the form of icons with the position of each icon on the GUI representing the location of the corresponding component on the mounting frame. One library for example can contain pre-designed flow schemes and component combinations from which the user can select a particular flow scheme or portion of a flow scheme. A further library can contain additional icons for components to be added to a flow scheme at the choice of the user, in a "drag-and-drop" manner. If a fluidics scheme has been selected from an embedded library in the monitor or the desktop computer, or has been devised by the user, the GUI can show the tubing connections needed to form the desired fluidics scheme.

Software can also be included for guiding the user to properly install fluid lines, i.e., tubing connections, between the various modules, and optionally to inform the user of any incomplete or missing connections. For proper functioning of the entire system, all of the proper fluid connections must be made, a process known as "plumbing" the system. When done manually, the making of such connections is a time-consuming process and prone to error. In certain embodiments of this invention, the plumbing process is simplified and the risk of error is reduced by inclusion of a "click-and-plumb" function in the software. Such a function can identify the proper connection sites for each fluid line one at a time and display the connection sites in a manner that will allow the fluid connections to be made in sequence.

The array of connections representing the flow scheme for the entire system can be displayed as a diagram of the system, showing the route of fluid flow between modules in a graphical format. A tubing connection between two modules within the graphical representation can be "clicked" (i.e., by a mouse or otherwise) to cause the system to turn on indicator lights on the modules themselves near the two locations between which a tubing connection should be installed. Once the user installs the tubing connection, another click by the user can turn off the indicator lights for that connection and turn on two different lights representing the next connection. Any type of light indicator can be used; of these, LEDs are often the most convenient. Alternatives to lights being turned on or off are lights changing color; indeed, any visual clues can be used, as will be apparent to the skilled software engineer. This click-and-plumb process can continue until all of the tubing connections are made. The system is then fully plumbed and ready for operation.

An alternative to using LEDs or other indicator lights on the modules for the click-and-plumb process is to use computer graphics that show a diagram or picture of the flow scheme as a display on a computer monitor or touch screen, the display containing virtual indicator lights that correspond to each of the sites for the tubing connections. The click-and-plumb process is performed by the individual in an analogous manner, except that the virtual indicator lights, rather than lights on the modules themselves, will turn on to indicate the connections to be made and then off to indicate that they have indeed been made. Certain embodiments will include both a display with virtual indicator lights and actual indicator lights on the modules, offering the user a choice between the two. Tubing connections can also be shown by means other than, or in addition to, indicator lights. The system diagram may thus show the connection points but not the tubing until each tubing connection is made, in which case the appearance of a line connecting two points on the diagram is an indication that a successful and correct connection has been made between the connections corresponding to those points. Alternatives to the absence/appearance of the line representing the tubing connection are a change in color, a change from highlighting to absence of highlighting (or vice versa), a change from normal line intensity to a bold line (or vice versa), and a change from a blinking line to a steady line (or vice versa). Other alternatives will be readily apparent to those of skill in computer graphics.

The "click-and-plumb" function can be initiated by conventional software means, such as a selection on the system control screen or a menu selection. The active fluidics scheme described above can be replaced by a wizard interface and the selection of a "next" function, as these terms are known in computer software. Other equivalent means will be readily apparent to those of skill in the art. The "click-and-plumb" function can be operated through a touch screen affixed to the system or through a computer in proximity to the system, with a button or switch on the system to initiate and advance the function. The button or switch is particularly useful when the system is retained in a refrigerated environment and the computer is placed outside the environment.

As an alternative to the "click" portion of the function, the system can be programmed to automatically advance between plumbing locations at fixed time intervals. Sensors can also be installed on the system to detect tubing connections that have been made. Examples of such sensors are optical sensors, electrical sensors, and pneumatic sensors. The "click-and-plumb" function can also be used for checking that all fluid connections have been properly made. To do so, the system can identify the correct connections sequentially to allow the user to check and determine whether a tubing line has in fact been installed to make each connection. As in the installation function, the display of individual connections can be advanced manually or automatically. All of these functions can be performed either with indicator lights on the modules or with virtual indicator lights or tubing connection indicators on a monitor or touch screen display.

The overall software platform, whether embedded in the mounting frame or in a desktop computer or distributed between the mounting frame and a desktop computer, will also contain programs dedicated to operating the fluidics scheme hardware, including causing the fluid manipulation components to direct fluids to and from the chromatographic separation column by way of the selected flow scheme. This function will for example include energizing or de-energizing pumps, opening, closing, or rotating valves, and similar operations to implement protocols for processing samples and operating the column. When the mounting frame software includes a GUI, the GUI can also include demonstration protocols that can be run both with and without attachment to the instrument, i.e., with and without any components having been engaged, to show the user how the system operates and how it generates and analyzes a chromatogram. In certain cases as well, the GUI will contain help files to assist the user in the setup and calibration of the instrument, the reading of component specifications, the design and programming of fluidics schemes and protocols, and troubleshooting.

As mentioned above, a single fluidics system consisting of modules mounted to a mounting frame equipped with a touch screen monitor can be termed a "workstation," and two or more such workstations can be independently operated and controlled by a common desktop computer external to the mounting frame or base unit. Each workstation can be powered independently, or a power distribution unit can be used with ports for multiple workstations. In either case, workstations can be added to or subtracted from the desktop computer without the need for additional wiring.

Software suite in external computer. When a desktop or other external computer is used, it can include a software suite that includes major chromatography functions and that can be configured to operate at any scale from an analytical or laboratory scale to a preparative scale, with additional functions appropriate to the scale of operation. Components of the software suite can include administration software, method editor or programming software, system control software, and evaluation software. Examples of functions that can be performed by these software components are as follows.

Administration software. Administration software can include a multi-level access system for different levels of authority and control. As an illustration, the access system can have five levels including administrator access as Level 1, supervisor access as Level 2, scientist access as Level 3, operator access as Level 4, and restricted user access as Level 5. When multiple workstations are connected to a single external computer, an administrator can use administrator access to name and create users for each workstation, or supervisors who will in turn name and control users through the supervisor access. Through the user access, a user can then view all workstations on which that user has been designated, and select a particular workstation on which a run is to be performed. Scientist and restricted user access can be used to establish other levels of access and use. Data generated by a workstation can be stored in a database management system which is either on the same computer in which the software suite is loaded or on a remote or external computer owned by the user and accessed through SQL (structured query language) or other such authentication. Databases in either the workstation or the external computer can contain data tables that can be extended, modified, and rapidly sorted through so that the data can be rapidly retrieved, exported, and backed up as desired.

An optional feature of the administration software is an ability to establish audit trails and electronic signatures for compliance with 21 CFR Part 11 regulations as promulgated by the Food and Drug Administration and published in the Federal Register of Mar. 20, 1997, Vol. 62, No. 54. Further optional features, of particular interest in industrial environments subject to regulatory review, are the inclusion of verification and validation protocols in the form of IQ/OQ/PQ (installation qualification, operational qualifications, performance qualifications) procedures, and the ability to generate a final report summarizing and referencing all protocols, results, and conclusions.

Method editor software. With this software component, a user, whether an individual or a group of individuals, can create a method either through a project folder or through a start menu. Methods can be created by sequencing groups of steps referred to as phases, using a pre-programmed method template. A method can also be created by modifying an existing method. Regardless of how a method is created, the software can include a prompt to the user offering the option to save the method prior to starting a run. A user creating such a method will be able to define the method settings, such as the parameters to be used for that method and a method outline. These method parameters and results can then be saved in a database where they are linked to the method from which they are generated. Parameters of the method can include the following:

Chromatography mode, examples of which are anion exchange, cation exchange, mixed-mode ion exchange, size exclusion, hydrophobic interaction, affinity, and isoelectric focusing Column parameters and requirements, examples of which are physical dimensions, pressure limits, flow rates, connector types, and part numbers Operational limits, examples of which are maximum pressure and minimum flow rate Selected operational parameters, for example the means of expressing elution flow volumes or rates, such as by number of column volumes, linear velocity, volumetric velocity, or simply time; buffer blending to achieve dilution, pH adjustment, and pH or concentration gradients The method outline will allow the user to create a sequence of phases, which are groups of logical steps that are common to chromatography procedures in general. Examples of such steps are equilibration, sample application, column activation, column washing, elution, column preparation, system preparation, and column performance tests. As noted above, these phases can be stored in a library, and the selection of phases or of groups of phases from the library, and the assemblage of selected phases or groups into a chromatographic protocol, can be performed by the user through the GUI. Each phase will have its own default operational parameters, modifiable by the user. Parameters for an equilibration phase, for example, can include flow rate, buffer salt concentration, buffer gradient, equilibration time, and buffer volume. Parameters for sample application can include manual application, application through a sample pump, application either through a sample loop or directly onto the column, and application through an autosampler, and protocols for washing the sample loop and for fraction collection, which can include parameters for fraction differentiation, for the means of fraction separation, for fraction destinations, and for fraction detectors. Parameters for column washing can include flow rates and the selection, concentration, gradient, and amounts of wash buffer to be used. Parameters for elution can include choices between isocratic elution, linear gradients, stepwise gradients, and gradient curves. Parameters for column preparation can include the choice of equilibration solution, the volume of solution to be used, the solution flow rate, and the incubation time. Parameters for system preparation can include selection of buffers, concentrations and quantities for priming the system tubing and inlets with buffer solution and the choice of inlets, outlets, column positions to be prepared, and incubation time. Parameters for a column performance test can include a choice of blank (non-absorbing) liquid or solution to pass through the column and the condition of the column during the passage of the liquid or solution, to determine such factors as height equivalent to a theoretical plate (HETP) and peak asymmetry factor (As). Further phases for possible inclusion can include column clean-in-place and system clean-in-place functions, for removing residual or non-specifically bound species without removing the column from the column rack or from the tubing connections between it and the modules.

The method editor software can contain pre-programmed methods supplied with the instrument, which can serve as templates for modification by the user. Examples are methods of system preparation, column clean-in-place methods, system clean-in-place methods, column performance tests, column preparation, column desalting, and methods specifically designed for particular chromatographic techniques such as affinity chromatography, anion exchange chromatography, cation exchange chromatography, chromatofocusing, gel filtration (size differentiation), hydrophobic interaction chromatography, and reverse-phase chromatography.

The method editor software can also include scouting functions, by which the system systematically varies one parameter of a phase and runs the variations in sequence to determine the optimal value of that parameter for a particular procedure. Systematic variations of this type are useful in screening columns, identifying an optimal pH, identifying a maximum sample volume for a particular column, identifying an optimal flow rate for a particular column, and identifying an optimum gradient length, slope, or stepwise configuration. Scouting parameters to be selected by the user can include column volume, flow rate, column pressure, flow-through fraction size, eluate fraction size, and peak fraction size. Once optima are obtained, the user can design experiments by creating a series of run conditions for a particular procedure to be performed on the instrument. Commercially available software packages that performed this function can be incorporated, such as MODDE of Umetrics Inc. (San Jose, Calif., USA) and JMP software of SAS Institute Inc. (Cary, N.C., USA).

A method once configured is run on any system that is available on the network with the appropriate configuration.

The software automatically maps the fluidics scheme in the method against the devices (i.e., the fluid manipulation components) that are installed on the mounting frame and notifies the user in case of discrepancies. In case of ambiguity or when multiple devices of the same type are present, the user is able to associate the physical location of the device with the corresponding location in the fluidics scheme. The user has the option of writing additional descriptive information to a particular run, of scheduling runs to be performed in sequence, of delaying runs or setting times for runs to be performed, of activating evaluation procedures, and of recording run data and results.

System control software. The system control component of the software suite enables the user to start, monitor, and control a run. Monitoring can include viewing the number of experiments in a queue and the experiment in progress relative to the queue, the phase and step of the method that is in progress, the time left for the phase/step to complete, the total time for the run to complete, and chromatograms completed and in progress. Monitoring can also include extending or stopping a run. As noted above, the system control software can include a fluidics library, which is a library of configured components and replacement components. The user can select a fluidics scheme from the fluidics library or modify the selected scheme (or create one's own) by adding or substituting components from the replacement components library. The software can be programmed to indicate when a component is incorporated into a fluidics scheme, to calculate dead volume associated with connective tubing, or to allow the user to enter the length of the tubing and then to calculate the dead volume based on the entered lengths. The software can automatically map the fluidics scheme in the method against the available devices present and notify the user in case of discrepancies. In case of ambiguity or when multiple devices of the same type are present, the user is able to associate the physical location of each device to its corresponding location in the fluidics scheme. During a run, the system control software can display the fluidics scheme flow path and monitor signals and parameters of each component in the scheme. The software can also be programmed to allow the user to alter operational parameters such as flow rate, pH, and pH gradient, and to do so directly on the displaced fluidics scheme during a run. The software can also be programmed to operate a run manually, selecting all run parameters independently of any of the pre-programmed methods. The chromatogram generated during a manual operation as well as the sequence of commands used to execute the manual run can be saved. The sequence of commands saved can be replayed as a manual method with or without modification.

Monitoring of a run can include displaying active flow paths throughout the performance of the run. This can be achieved with the same LEDs or other indicator lights that are used for the click-and-plumb operation, whether the lights are on the modules themselves or are virtual lights or tubing segments on a diagram displayed on the computer screen. As in the use of computer graphics in the click-and-plumb operation, an active flow path can indicated by the appearance of a line, otherwise absent from the display, representing a tubing segment, a change in color or intensity of such a line, or a change from a blinking appearance to a continuous appearance. Many flow schemes contain multiple pumping systems, including for example a two-pump combination arranged to produce a gradient flow of buffer solution plus a sample pump to prime a sample loop or to feed sample directly to a column. The fluid line leading to or emerging from any one pump will be indicated by indicators on that line or at the two extremities of the line. When both pumps on the gradient flow system are in operation, indicators on the output lines from each pump will show those lines to be in the active mode, and when the system progresses from one stage or function of the operation to another, the display will show the change in active flow path. The indicators will thus enable the operator to see the system's stage of operation in real time. In the event of a programming error within the method, the indicator lights can alert the operator that flow is occurring in locations where flow was not intended, thereby allowing the operator to rewrite the program and thereby correct the error. In the event of a fluid leak during operation, the indicator lights can direct the operator to only those locations where fluid should be flowing. This will help the operator to find the location of the leak.

In addition to the functions described above, the system control component of the software suite can include a function that displays the potential fluid paths for pumps that are included in the flow scheme. This function can be used to display the path along which a particular pump when operating would cause fluid to flow, Such information would be useful in ensuring that fluid will go where intended once the pump is started. The indication of an undesired flow path would inform the user of an improper connection having been made, and thereby allow the user to correct the error. This type of indication can be distinguished from indications representing click-and-plumb operations or active flow paths, for example, by using different colors, different intensities or line widths, different types of lines (dotted or dashed vs. solid, for example), or different signals (flashing or blinking vs. steady, for example). Here again, the indication or signal can be generated by LEDs on the modules themselves, or indications on a diagram on the computer screen, such as virtual LEDs or lines representing tubing segments.

A further function that can be served by indicators on the modules or on a computer screen is to show the locations of ports where manual injection can be made, either by syringe or other means, and the flow paths that the fluid will follow once injected through those ports. Manual injection is often used for filling a sample loop or for calibrating a pH meter, for example. The indicator can help the user select the correct port for a particular injection.

A still further function that can be served by indicators is to indicate the positions of rotary valves. A rotary valve will often be rotatable between two or more positions that either direct the fluid passing through the valve to different flow paths downstream of the valve or that receive fluid from different sources or incoming lines to the valve, or both. Rotary valves can thus switch the system between sample loop priming, sample injection, the flow of an elution buffer solution through a column, and washing the sample loop or other parts of the system with wash fluid, and also in many cases stopping flow or rerouting the flow around the valve. Certain users will wish to know the position of a valve at a particular point in time, either to check to see if proper connections have been made or to trouble shoot a flow problem or aberration in the system operation. The position of the valve, as well as the ports of the valve that are in an active flow path, can be indicated by any of the methods listed above.

While some or all of the functions listed above can operate simultaneously by use of distinguishable signals and/or distinguishable changes in signals, it will be most convenient in certain embodiments of the invention include means within the software to allow the user to select the functions to be displayed.

When a diagram on a computer monitor is used for any of the reasons described above, the diagram can be a layout of the actual configuration of the system components and flow paths, or an abstract or simplified representation of the configuration. Abstract or simplified representations are advantageous due to the ease by which they can be followed. A typical abstract representation arranges the primary flow path components in a horizontal line with the different components represented by distinct icons, the components joined by lines representing tubing connections. Boxes above particular components can include information relating to the component such as flow rate, temperature, pressure, volume, and other parameters.

The system control software can also be programmed to calibrate modules, such as pumps, conductivity flow cells, pH probes, fraction collectors, and auto-samplers, as well as to record and log all calibration events. Auto-calibration upon start-up can also be an option, including stepwise instructions to the user. Diagnostic functions for the various components and modules can also be included. Components that can send error signals include air sensors, auto-samplers, fraction collectors, pH probes, UV lamps, conductivity monitors, pumps, and valves. The number of times a component has been used and the length of usage time can be recorded and compared to the maximum number of uses or length of use time which can be included in the data supplied by the microcontroller associated with the component. A warning signal can then be generated by the system control software to instruct the user to replace or regenerate the component.

Further features that can be included in the system control software are a method validation capability and a service log. The method validation capability can allow the user to view a simulation of the fluidic path and an animated progression of a run prior to performing an actual run. The service log can record times of actuation and deactuation of components that are susceptible to aging upon use such as UV lamps, pH probes, filters, and pump seals. The service log can also contain a record of servicing events. The system control software can also enable the user to manually override a programmed method, such as by stopping or pausing a pump, resuming operation of a stopped or paused pump, keeping a pump operating beyond a programmed operation interval, starting and stopping a fraction collection, proceeding forward to a subsequent step in the protocol, and any of various further commands and options within an individual override operation.

(4) Evaluation software. Evaluation software can serve a wide range of functions, including displaying results, analyzing data, quantifying and calibrating results, comparing peaks with each other and chromatograms with other chromatograms, comparing samples, preparing and customizing reports, and importing and exporting data.

The results can for example be in the form of chromatograms that are either displayed on the GUI or recorded in a printout. Data analysis can include such functions as peak integration, measuring, analysis, and identification, peak mapping, baseline determination, and any other parameters associated with peaks, valleys, and baselines. Quantification and calibration can include calculations of area percentages, relative heights, calibrations for variations in sample size and sample preparation, curve fitting, and peak origin treatments such as recording an origin location and placing the origin at a selected location. Performance calculations can include retention times, actual or relative, number of theoretical plates in absolute terms or per unit column length, column capacity factors, peak symmetry or asymmetry factors, peak widths, and molecular weight estimations based on retention times on a size-exclusion chromatography (SEC) matrix compared to standard curves. Chromatogram and peak comparisons can include differentiations by color, line quality, or size, and the addition of legends. Report preparation and customization can include standard and custom formats and scale adjustments. Importation and exportation of data can include choices of spreadsheet formats such as Microsoft EXCEL, WORD, POWERPOINT, and pdf, and the capability of sending or receiving data from other computers or software.

Methods and runs saved in the database can be searched and retrieved through a browser. A search can be filtered so that searches made through the method editor can allow users to view the list of existing user methods or method templates, whereas searches performed through an evaluation editor would allow the user to view saved runs through a list of thumbnails or chromatograms. Multiple runs can be selected in the browser, reviewed individually and transferred directly into a "compare run" field under the evaluation editor through a single mouse click.

Figure 1A:
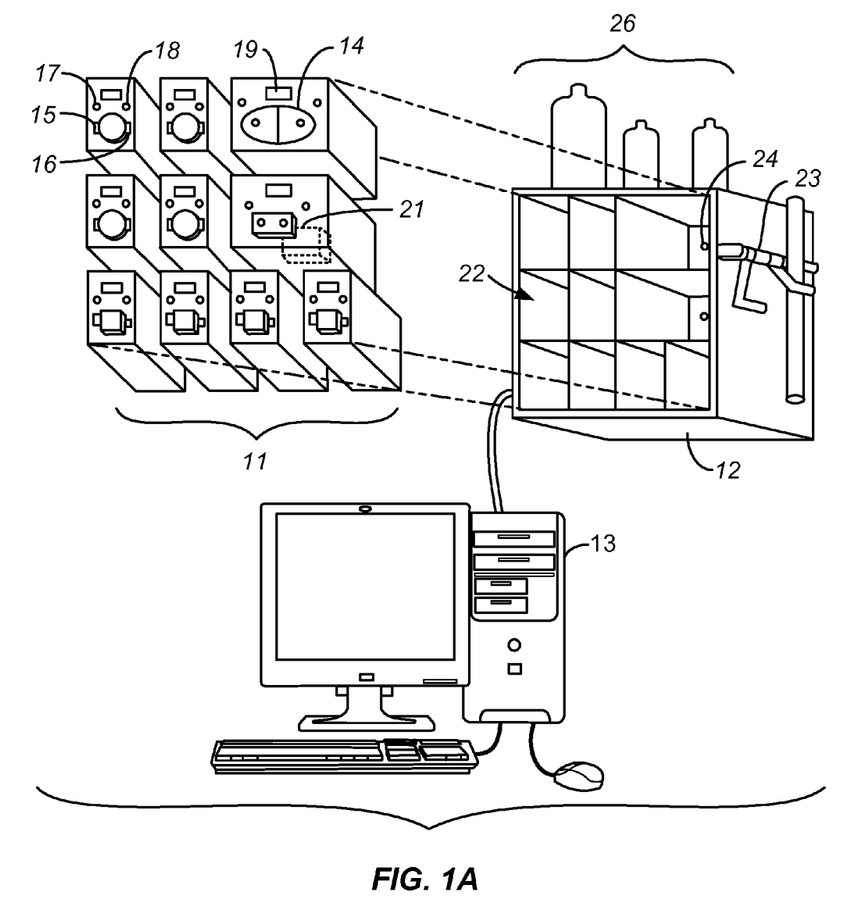
FIG. 1A is perspective view of a modular chromatography system in accordance with the present invention with components separated for ease of viewing.
Figure 1B:
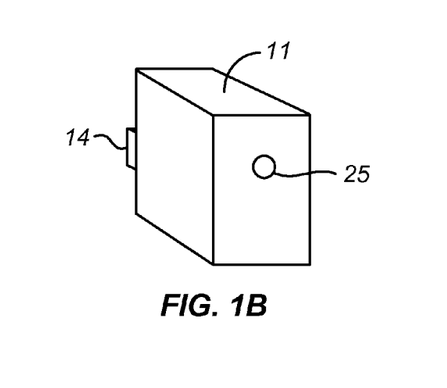
FIG. 1B is a view of one module of the system of FIG. 1A, shown in perspective from the rear.

FIG. 1A is a representative illustration of the principal components of one example of a modular chromatography system in accordance with the present invention. A series of modules 11 are shown separated from each other for ease of viewing and poised in front of a mounting frame or base unit 12 which is connected to a computer 13 containing the software platform that operates the system. Each module 11 has a fluid manipulation component 14 which includes a fluid input 15 and a fluid output 16, both of which are accessible from the front end of the module. Positioned on the front end of the module itself, or at least visible from the front end, are a fluid input connection indicator 17 and a fluid output connection indicator 18, to guide the user in making fluid connections between the modules. Also positioned on the front end of the module, or at least visible from the front end, is an additional indicator 19 that can serve as a status indicator, data indicator indicating operational information pertaining to the fluid manipulation component, or an alarm indicator, or individual indicators for each of these functions. Alternatively, any of these indicators 17, 18, 19 can also be on the fluid manipulation component rather than the front surface of the module. In the interior of each module or exposed at the rear end of the module is a microcontroller 21. The mounting frame 12 has a series mounting sites in the form of bays 22 to receive the modules, and a column rack 23 on one side of the frame. Two of the bays (in the upper right corner and the right end of the middle row, respectively) are double-wide to accommodate double-wide modules. As explained above, the Figure is merely an example; the number of modules and bays can vary widely, and the frame can be designed to allow additional rows to be added. Each bay 22 contains an electrical connector 24 to send signals to, and receive signals from, the microcontroller 21 in any module that is inserted in the bay. FIG. 1B shows the reverse side of one module 11, with the exposed microcontroller connection 25 that will contact the connector 24 in each bay 22 of the base unit. Reservoirs 26 (FIG. 1A) for liquids such as elution buffers and wash liquids are placed in an accessible location, in this case atop the base unit 12. Lengths of tubing, not shown, connect the various fluid manipulation components 14 to each other and to the columns in the column rack 23 as well as the reservoirs 26.

Figure 2:
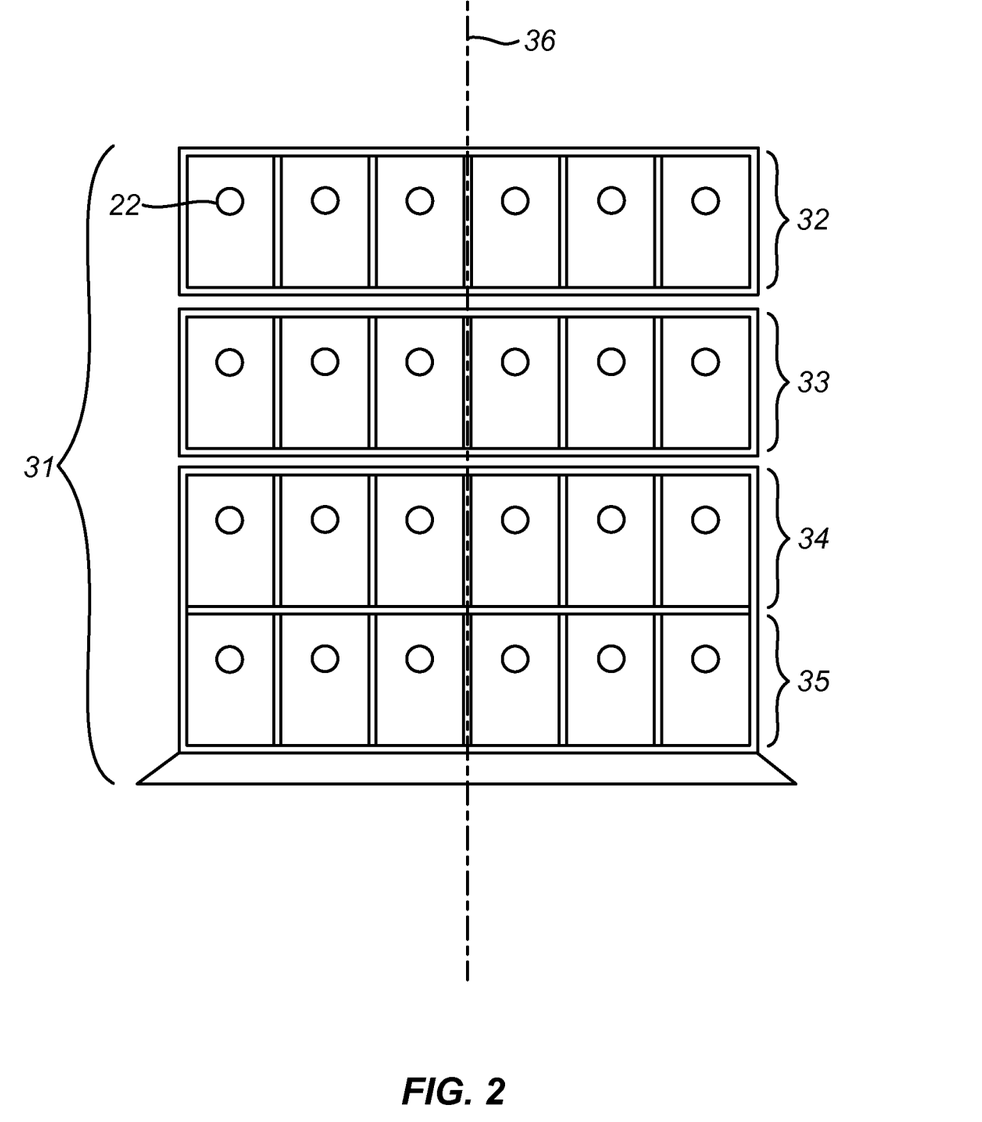
FIG. 2 is a front view of a base unit in accordance with the invention as an alternative to the base unit of the system of FIG. 1A.

FIG. 2 is a front view of a base unit 31 (mounting frame) that is similar to the base unit 12 of FIG. 1 except that the base unit of this Figure includes four rows 32, 33, 34, 35, alternately referred to as "stories," and the upper two stories 32, 33 are rotatable relative to each other and to the lower two stories 34, 35. The rotation is about a vertical axis 36 passing through the centers of each of the four stories.

Figure 3:
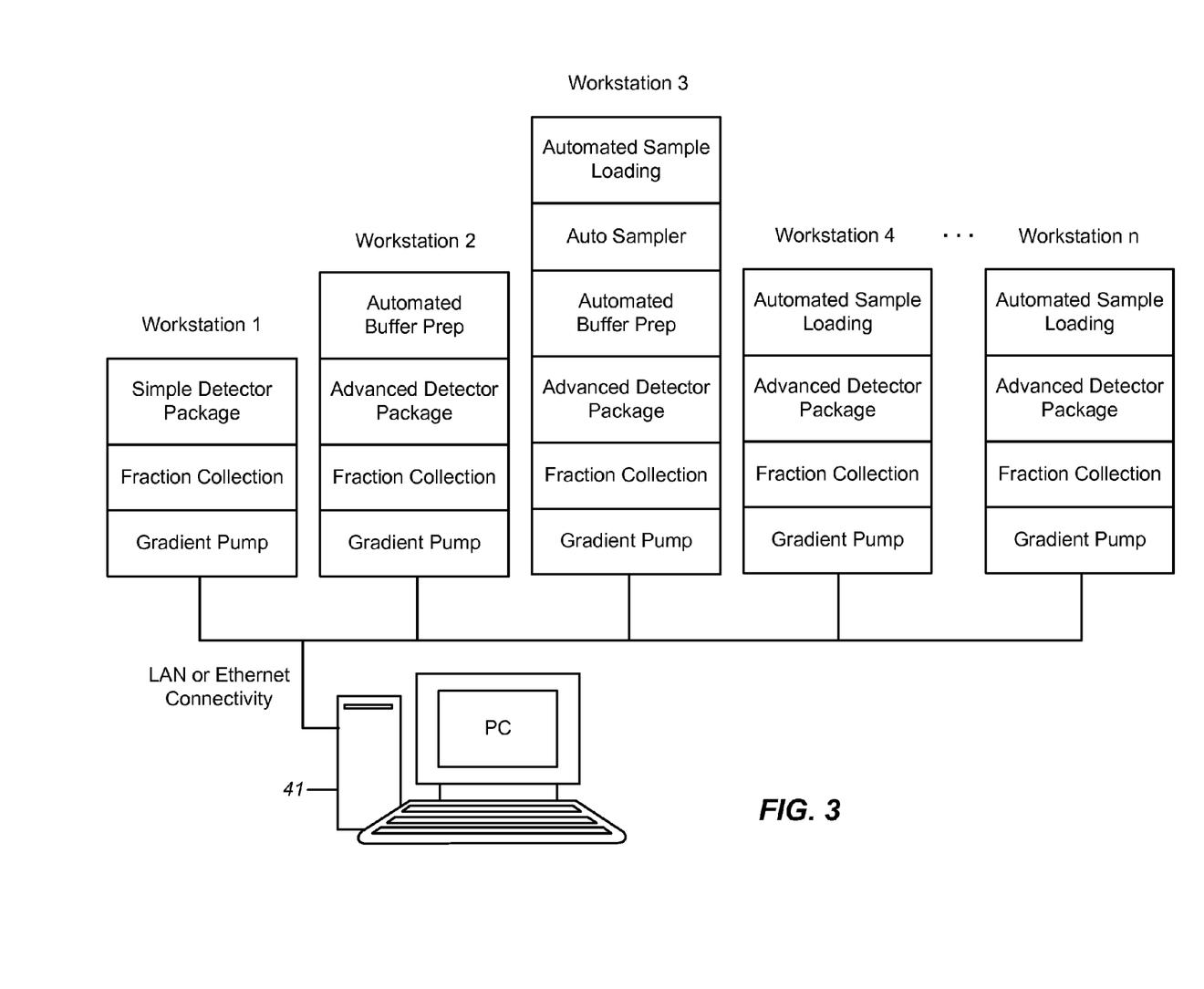
FIG. 3 is a diagram of a system in accordance with the present invention with multiple workstations.

FIG. 3 shows the system topology of an example of a chromatographic system with multiple work stations that utilizes features of the invention. Each workstation corresponds to one set of modules 11 and one base unit 12 of FIG. 1A (or base unit 31 of FIG. 2), and each workstation has its own combination of modules, with the fluid manipulation components of the modules being sample loading components, sample loops, buffer preparation components, detectors, fraction collectors, and gradient pumps, as shown. In this multi-workstation system, a single computer 41 controls the entire group of workstations. The components and fluidic connections in individual workstations will be selected by the user from a library supplied with the computer program or will be custom designed by the user.

Figure 4:
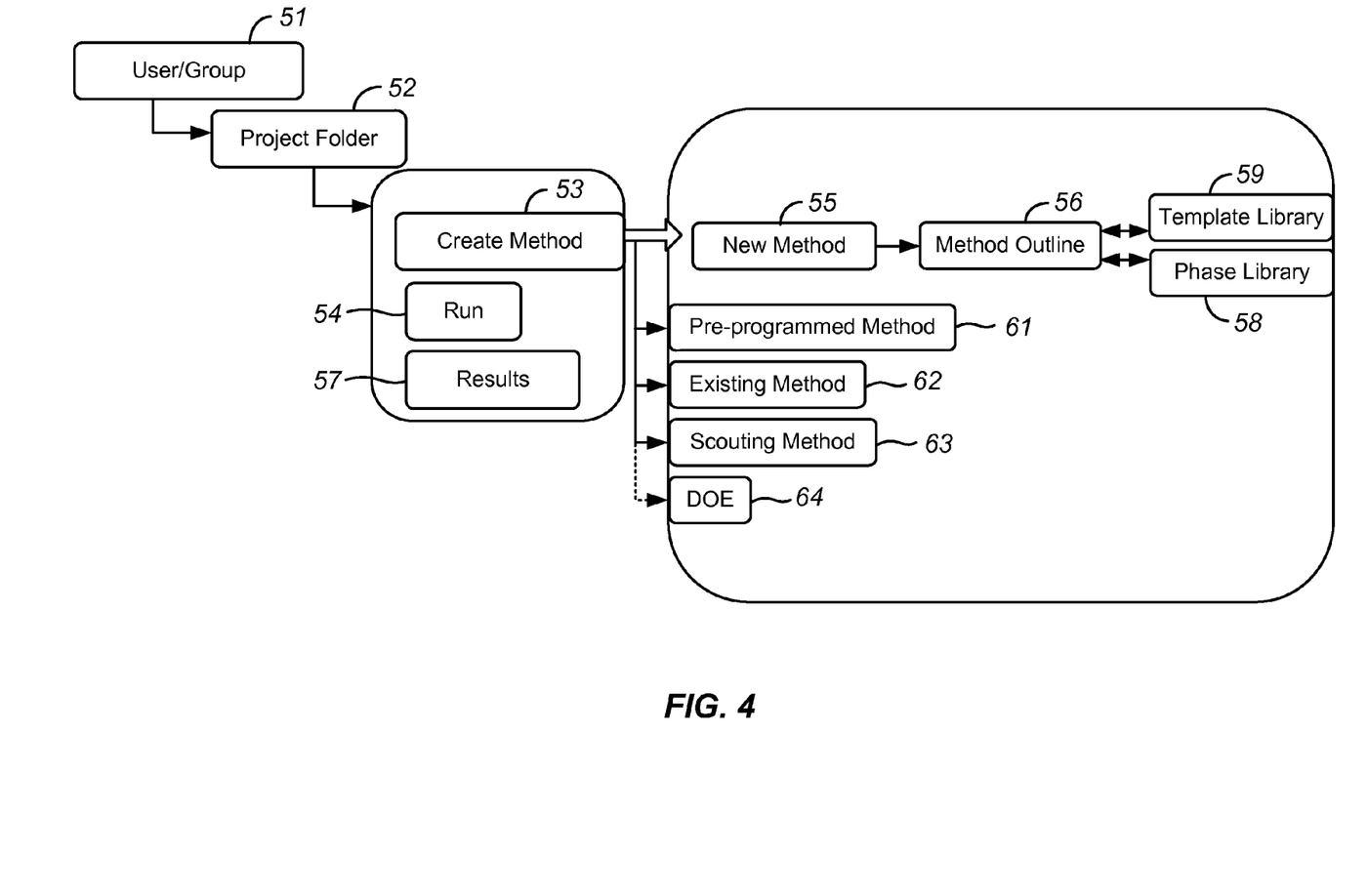
FIG. 4 is an outline for a computer program for use in the invention.

FIG. 4 is an outline of one example of a computer program for a "Method Editor" in accordance with the invention to be used in selecting, designing, or modifying a fluidics scheme for a single workstation. As an example, a user or a group member 51 (where access is limited to a group of designated individuals) can "create" a "method" 53 either through a "Project Folder" 52 or through a "start" menu, both incorporated in the computer software. The user is then prompted to save the "New Method" at any point prior to starting a "Run" 54. When the user creates a "New Method" 55, the user can define the method settings, which include the parameters to be used for that method in addition to defining the "Method Outline" 56 that is to be run. The "Run" 54 and "Results" 57 for that method can be saved by the user in a database where they would be linked to the "New Method" 55 that was used to generated them.

A user can define a method in various ways, including the use of (i) a phase library 58 or a template library 59, (ii) a pre-programmed method 61, (ii) a protocol 62 previously created and saved by the user, (iv) a scouting method 63, or (v) a "Design of Experiments" (DOE) method 64. A graphic representation of the method being programmed is displayed, allowing the user to make and view changes to each step of the method in both graphical and tabular mode. Parameters that can be defined in the design of a method can include the following:

Technique: The user can select from a list of common chromatography techniques, such as anion exchange, cation exchange, mixed mode ion exchange, size exclusion, and hydrophobic interaction chromatography. These options can be listed under a "Technique" heading. The software can also permit the user to add new techniques if needed. For fluidic diagrams requiring multiple columns, the user can select the column for which to set the parameters.

Column type: This enables the user to select from a list of options for columns from a column library, including competitive columns in different column sizes corresponding to the technique selected. Columns with RFID tags can insert setup information from the tags into the fluidics diagram. For fluidic diagrams requiring multiple columns, the user can assign each column type to its appropriate position in the diagram. The software can supply default parameters such as pressure limits, flow rates, etc., based on the column selected, modifiable by the user. The software can also provide guidance, such as connector type and part numbers.

Maximum Pressure: A recommended pressure limit that is slightly below (by 1% or a user-defined amount) the maximum pressure of the column will be displayed. The user then has the option to enter a value different from the recommended value. For values higher than the maximum recommended pressure, a "caution" prompt will appear, asking the user to confirm if the value entered is correct. The system can then modulate the flow rate once the pressure threshold has been reached in order to maintain the pressure at or slightly below the set pressure threshold.

Minimum flow rate: The minimum flow rate capacity of the pump can be set as a default minimum flow rate for a column fed by the pump. The user can then have the option of entering a value different from the default. The user can also have the option of selecting the flow rate units.

Elution parameter: The user can program methods in any flow mode, such as number of column volumes, total volume, or time. A method created for a small column should scale automatically to maintain the same linear flow rate when a larger column is used for the same method.

Buffer Blending: This feature will enable the user to dilute a buffer, or to define either a single point pH or a pH gradient and duration during an elution and select a buffer to achieve the desired pH or pH gradient.

The phase library 58 enables the user to create a "Method Outline" 56 consisting of a sequence of phases such as equilibration, sample application/collection, column wash, elution, column preparation, system preparation, and column performance test. The user can "drag-and-drop" groups of individual phases from the phase library 58 into the method outline, and each phase may be used once or multiple times in a method outline. Custom phases can also be created and added to the phase library. The template library 59 is a library of templates, i.e., groups of phases that are frequently used together. Parameters for each phase within a template can be modified by the user once the template is added to a method. The steps and parameters being used within each phase are displayed, and the default parameter values can be altered if desired. Default flow rates or column volumes in the phases would be set based on the type of column defined by the user. For a column not included in the library, the user can enter the parameters manually.

Equilibration: This phase equilibrates the column before purification or re-equilibrates the column after purification. The user can define the concentration and volume of buffer to be used for equilibrating the column. Equilibration can also be set to proceed until a certain detector condition such as a threshold or stability of detection (conductivity, UV, or pH) has been achieved.

Sample Application: The phase applies sample to the column. For sample application, the user selects the sample injection technique, for example manual injection, injection by use of an auxiliary sample pump either through a sample loop or directly onto the column, or injection by the use of an autosampler with the user specifying the loop or vial type and volume, the sample volume, and the buffer used for sample injection. For sample collection, the user can define how the fractions are collected, either with the use of a fraction collector, outlet valves, or waste. Further options include the fraction destination, i.e., the type of rack or the vial or well position where the fractions are to be collected, the collection pattern (S vs. Z), and whether fraction collection is to be based on fixed volume, peak fractions, or a combination of the two. Peak fractions can be based on peak slope and/or threshold. For thresholds, the start and end thresholds can be selected. Software can be used that can combine slope and threshold to determine when a peak is ascending or descending, and that can detect valleys, peaks, and peak maxima to ignore noise in the chromatogram. For multiple sample injections and sequential runs, the software can notify the user when the total collection volume is greater than the total elution volume of all the experiments added. Software can also be programmed to track peaks to the fraction in the tube. Peak fractions can be displayed by selecting a peak on the chromatogram or selecting a fraction tube. The selected peak and the corresponding tube containing that fraction should be easily identifiable such as by color.

Column Wash: This phase washes the unbound sample from the column after sample application or removes strongly bound proteins after elution. Parameters that can be defined for this phase include flow rate, if different from the flow rate in the method setting, wash buffer, and length of wash. The length of wash can be defined either in column volumes or until a certain detector condition is met, such as a stable conductivity or a pH or UV value.

Elution: This phase elutes the sample from the column. Parameters to be defined include the elution and fractionation settings. Elution techniques can be selected from the following options: (a) isocratic (i.e., elution with a constant eluent composition, which is commonly the same composition as that of the solution used to equilibrate the column), in which the length of elution (in terms of the number of column volumes, volumetric flow rate, time, or volume) can be selected and a delay for fraction collection can be set if needed; (b) continuous gradient, including linear, concave, and convex gradients, in which the gradient concentration, length, and slope can be selected for linear gradients, and the gradient shape for concave and convex gradients; and (c) step gradient, in which one or more steps can be selected from a pull-down menu. An option to clean the column after elution with a selected volume and concentration of buffer, or to re-equilibrate the column after elution, or both, can be included, using conditions programmed in at the equilibration step. Step gradients can either be basic or advanced, in which the buffer concentration and length of the step in each elution segment can be individually selected. An option can also be included to flush the system with a set concentration and volume of buffer between steps and to vary the fraction volume within each elution segment.

Column Preparation: This phase prepares the column before use by removing any storage solution present in the column and equilibrating the column. The inlet position, buffer solution, volume, flow rate and incubation time are selected and the column is filled with buffer solution.

Column Clean-in-Place: This phase cleans the column after purification runs by rinsing the column with a cleaning solution to remove nonspecifically bound proteins. The inlet position, the cleaning solution volume, flow rate and incubation time are selected and the column is filled with a cleaning solution. For a column equipped with an RFID tag that records column pressure, a prompt will appear on the display when the column pressure becomes excessively high, instructing the user to perform Column Clean-in-Place. The Column Preparation phase and the Column Clean-in-Place phase can both be run either separately from any run or as phases within a run.

System Preparation: The System Preparation phase removes storage solution from the system tubing and inlet and fills the tubing and inlet with buffer solution before a run. The inlets, outlets and column positions to be prepared are selected and the system is filled with the appropriate buffer solution, with one buffer solution per phase.

System Clean-in-Place: The System Clean-in-Place phase cleans the system after purification runs by rinsing the system with cleaning solution. The inlets, outlets and column positions to be cleaned are selected and filled with the cleaning solution, with one cleaning system per phase. Three System Clean-in-Place phases, for example, can be included to allow three different cleaning solutions to be used. The System Preparation and System Clean-in-Place phases can both be run either separately from any run or as phases within a run.

Column Performance Test: The efficiency of a packed column in terms of height equivalent to a theoretical plate (HETP) and the peak asymmetry factor (As) are tested in this phase. After equilibration of the column, sample is injected via a capillary loop and eluted isocratically. A non-adsorbing sample such as acetone or salt can be used. After the elution, the HETP and As are calculated in an evaluation module.

Referring again to FIG. 4, the system can be equipped with pre-programmed methods 61 from which the user can choose, rather than creating a new method 55. Examples of pre-programmed methods, each of which can be accompanied by a buffer recommendation, are as follows.

Affinity Chromatography: After equilibration of the column and sample application, the protein of interest is adsorbed to the column ligand. The column is then washed to remove unadsorbed proteins and elution is performed either by using a buffer containing a competitor to displace the protein of interest, or by changing the pH or ionic strength. Elution in affinity chromatography is most often performed by a single-step elution, but can also be performed in two steps, the first to remove weakly bound material, which is often discarded, and the second to remove more strongly bound material. With either type of elution, the column is then re-equilibrated with start buffer.

Anion Exchange Chromatography: After equilibration of the column and sample application, negatively charged proteins are adsorbed to the column ligand. The column is then washed to remove unadsorbed proteins and elution is performed either isocratically or by using a gradient of increasing salt concentration, the gradient being either a step gradient or a continuous gradient. The column is then washed and re-equilibrated with start buffer.

Cation Exchange Chromatography: After equilibration of the column and sample application, positively charged proteins are adsorbed to the column ligand. The column is then washed to remove unadsorbed proteins and elution is performed either isocratically or by using a gradient, stepwise or continuous, of increasing salt concentration. The column is then washed and re-equilibrated with start buffer.

Chromatofocusing: After equilibration of the column and sample application, elution is performed using a pH gradient, causing the proteins to separate and elute according to their isoelectric points. The column is then re-equilibrated.

Column Clean-in-Place: The column is filled with a cleaning solution, inlet positions are selected, and the solution identity, volume, flow rate and incubation time are entered.

Column Performance Test: After equilibration of the column, a non-adsorbing sample such as acetone or salt is injected via a capillary loop and eluted isocratically. Values for HETP and As are then determined.

Column Preparation: The column is filled with buffer solution, inlet positions are selected, and the solution identity, volume, flow rate, and incubation time are entered.

Desalting: After equilibration and sample application, the proteins are eluted isocratically. This technique is commonly used for buffer exchange.

Gel Permeation Chromatography: After equilibration and sample application, proteins are separated and eluted according to size.

Hydrophobic Interaction Chromatography: After equilibration of the column and sample application using a buffer containing a high salt concentration, for example 2M $(NH_4)_2 SO_4$, hydrophobic proteins are adsorbed to the column ligand. The column is then washed to remove unadsorbed proteins and elution is performed either isocratically or using a gradient, stepwise or continuous, of decreasing salt concentration. The column is then washed and re-equilibrated with start buffer.

Reverse Phase Chromatography: After equilibration of the column and sample application, hydrophobic proteins adsorb to the column ligand. The column is then washed to remove unadsorbed proteins and elution is performed either isocratically or by using a gradient, stepwise or continuous, of a non-polar organic solvent such as acetonitrile. The column is then washed and re-equilibrated with start buffer.

System Clean-in-Place: The system is filled with cleaning solution and inlets, outlets and column positions are selected for cleaning. Three System Clean-in-Place phases for example can be included to allow the use of three different cleaning solutions.

System Preparation: The system is filled with preparation solution and inlets, outlets and column positions are selected for preparation. Two System Preparation phases for example can be included to allow the use of two different preparation solutions.

The option of using one of various existing methods 61 as shown in FIG. 4 allows the user to access methods previously run on the system. Once an existing method is selected, the user will able to save the method under a new name, either after having modified the method or using the method without modifications.

The scouting method 63 option allows the user to create a set of methods in which one parameter is systematically varied and to run the methods in sequence. Such scouting can be used for example to screen columns, to find an optimal pH, to test a column capacity in terms of sample volume, to optimize gradient length and slope, or to optimize step gradients. A pull-down menu can list different variables from which the user can select, as well as the number of runs for the scouting experiment. Examples of scouting variables are column volume, flow rate, column pressure limit, flow-through fraction size, eluate fraction size, peak fraction size, and linear concentration gradient and length.

A system that includes a "Design of Experiments" (DOE) software package 64 allows the user to vary multiple parameters at once and create a series of run conditions for a particular chromatography technique. The output can be imported into a DOE method synthesizer that will automatically output a series of experiments to verify the DOE design space. The user can be given the option to select the final number of experiments to be run and then execute the runs and produce a report that correlates the design output to the experimentally obtained results. Commercial DOE software packages such as MODDE and JMP (referenced above) can be used and integrated into the method editor so that the output from the DOE is generated into an executable method on the system platform.

Figure 5:
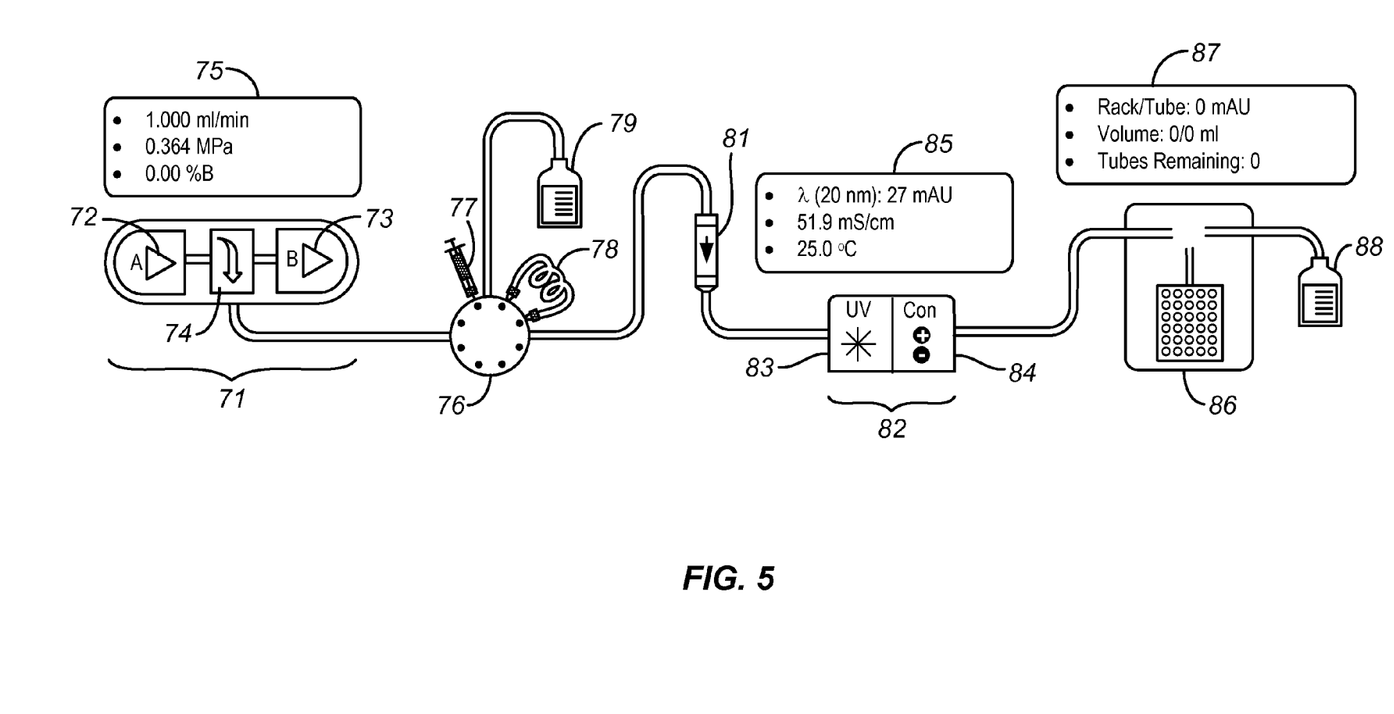
FIG. 5 is a screen shot, or graphical display, of one flow scheme that can be displayed on a monitor in accordance with the invention.
Figure 6:
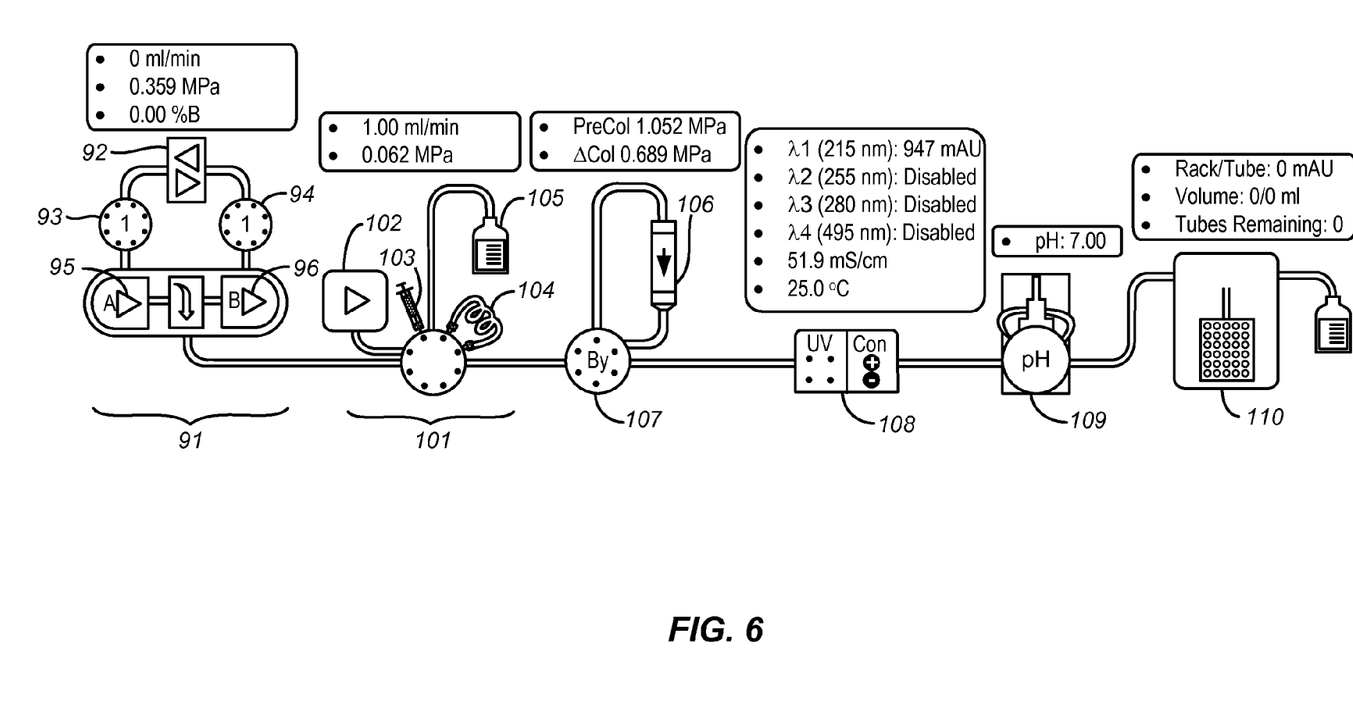
FIG. 6 is a screen shot, or graphical display, of a second flow scheme that can be displayed on a monitor in accordance with the invention.

FIGS. 5 and 6 are examples of graphical displays that can be used to represent flow paths and to indicate some of the operations and functions described above. Although the Figures are not in color, different colors or different color intensities can be used on the display to differentiate among active and inactive flow paths, pump-driven and manually drive flow paths, principal vs. bypass flow paths, and other operational information. Flow sensors can be installed on individual tubing segments on or between the modules themselves or on the modules themselves to confirm that the display is a real-time representation of the actual system. In each of these Figures, the components are shown in a generally linear arrangement with flow from left to right, each component is represented by an icon with the lines between the icons representing connective tubing, and a legend above each icon lists information pertaining to the component, such as its capacity, operating parameters, and current status. Certain fluid lines, such as lines leading to bottles of solutions, are eliminated to simplify the diagrams.

FIG. 5 depicts a flow path that begins with a gradient pump system 71 that includes individual pumps 72, 73 for buffers A and B, respectively, and a mixer 74. The legend 75 for the pump states the total flow rate, the pump pressure, and the proportion of buffer B as a volume percent of the combined flow at any point in time. Immediately downstream of the gradient pump system 71 is a rotary valve 76 to which are connected a manually operated syringe 77, a sample loop 78, and a waste reservoir 79 for excess sample during filling of the sample loop. Immediately downstream of the rotary valve 76 is a chromatographic column 81, whose outlet leads directly to a detector system 82 that includes a UV detector 83 and a conductivity detector 84. The legend 85 for the detector system 82 states the wavelength at which absorbance is detected by the UV detector and the absorbance being detected at any point in time, the conductance being detected in millisiemens per centimeter, and the temperature. Downstream of the detector system 82 is a fraction collector 86, and its associated legend 87 which states for any point in time the rack and tube in use at that time, the volume collected in that tube, and the number of tubes remaining unfilled. The final component shown is a waste reservoir 88 for fluids passing through the column 81 that are not diverted to the fraction collector 86.

One display scheme that can be used with the display of FIG. 5 is to show all connecting lines in a light or dull color until they are active when they change from dull to a bright intensity of the same color. The syringe 77 in this example can be shown in a different color, and any lines that are active when the syringe is in operation can likewise be shown in the same color as the syringe.

FIG. 6 depicts a flow path that includes more options than that of FIG. 5. The gradient pump system 91 in this scheme is shown with feed lines that include a four-way valve 92 to allow up to four different solutions to be blended together in any desired ratio. Between the four-way valve 92 and the gradient pump system 91 are two rotary valves 93, 94. The common port of one rotary valve 93 is connected to one pump 95 while the common port of the other rotary valve 94 is connected to a second pump 96, while port 1 of each rotary valve is connected to the outlet of the four-way valve 92. The two rotary valves 93, 94 allow each pump to deliver different solutions that are connected by fluid lines to any of the multiple ports on these valves. As stated above, neither bottles of solutions nor fluid lines from bottles of solutions to the inlets of the valves 93, 94 are shown. A sample injection system 101 includes a sample pump 102 in addition to the manual syringe 103, sample loop 104, and waste reservoir 105. The chromatographic column 106 is connected to a column selector valve 107 which can be used to select between multiple columns, only one of which is shown in this diagram, or to bypass all columns. In the diagram, the letters "By" when displayed indicate that the valve 107 is currently in the bypass position. A pH detector 109 is positioned between the UV/conductivity detector 108 and the fraction collector 110. Legends are associated with each component as in FIG. 5. The display scheme for the flow path of FIG. 6 can use different colors (blue and green, for example) to differentiate between the flow paths of the sample injection system 101 and the principal flow path extending from the gradient pump 91 through the column selector valve 107, detectors 108, 109, and fraction collector 110, with bright vs. dull color intensities to differentiate between active and inactive flow paths, and the color grey to indicate bypass routes. Other colors and methods of differentiation, such as dotted vs. solid lines and blinking vs. continuous lines, can be used instead or in addition to those states above, as will be readily apparent to those of skill in the art of computer displays.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A system for joining a plurality of fluid manipulation components into a flow scheme for directing fluids to and from a chromatographic separation device and for operating said joined fluid manipulation components according to a selected protocol, said system comprising:
  a plurality of modules, each said module comprising (a) one of said fluid manipulation components and (b) a microcontroller that (i) encodes machine readable data characterizing the type of said fluid manipulation component, and (ii) transmits operational signals to said fluid manipulation component in response to commands received from outside said module;
  a mounting frame comprising a plurality of mounting sites, each said mounting site constructed to receive a single module interchangeably with other said modules, and each said mounting site comprising a signal connector that couples to and communicates with the microcontroller of a module mounted at said mounting site; and
  a software platform embedded in said mounting frame or in a computer external to said mounting frame or distributed between said mounting frame and a computer external to said mounting frame, the software communicating with the microcontroller of each module mounted on said mounting frame through said signal connectors, said software being programmable for (1) receiving said machine-readable data, (2) recognizing from the received machine-readable data the types of the fluid manipulation components, (3) automatically mapping the plurality of fluid manipulation components to the flow scheme based on the received data, (4) guiding a user of the system in the joining of said fluid manipulation components according to said flow scheme, and for (5) causing said fluid manipulation components, once joined, to direct fluids to and from said chromatographic separation device in accordance with said protocol.

2. The system of claim 1 wherein each said microcontroller further (iii) detects malfunctions of said fluid manipulation component and emits an alarm signal in response to said malfunction.

3. The system of claim 1 further comprising a monitor that graphically displays fluid connections between the fluid manipulation components of the modules mounted to said mounting frame in accordance with said flow scheme.

4. The system of claim 3, further comprising means for indicating where fluid connections are needed for individual segments of said flow scheme.

5. The system of claim 4 wherein each said module further comprises indicator lights for tubing connections and said means for indicating where fluid connections are needed includes said indicator lights, said indicator lights being responsive to said software.

6. The system of claim 3 wherein said software comprises a software suite that comprises means for monitoring a run being performed on said system by displaying on said monitor all active flow paths during said run.

7. The system of claim 6 wherein said software suite further comprises means for displaying chromatographic data produced by a run performed on said system.

8. The system of claim 7 wherein said chromatographic data is one or more members selected from the group consisting of peak integration, peak measuring, peak identification, peak mapping, and baseline determination.

9. The system of claim 2 wherein each said module further comprises a data indicator indicating operational data pertaining to the fluid manipulation component on said module.

10. The system of claim 2 wherein each said module further comprises a visual alarm indicator and said alarm signal produces a visually observable change in said alarm indicator.

11. The system of claim 1 wherein said mounting sites are bays into which said modules are inserted, and said signal connectors are affixed to interior walls of said bays.

12. The system of claim 1 wherein said mounting sites are bays arranged in a two-dimensional vertical array of rows and columns, all bays opening to a common side of said mounting frame.

13. The system of claim 12 wherein said bays comprise subgroups of bays, including a second subgroup whose bays have widths that are multiples of the bays of a first subgroup.

14. The system of claim 12 wherein said mounting sites comprise bays separated by barriers which are removable such that adjacent bays can be combined to result in a single bay of dimensions equal to the sum of said adjacent bays.

15. The system of claim 12 wherein one or more of said rows is immobile relative to said mounting frame and one or more of said rows other than said immobile rows is rotatable about a vertical axis.

16. The system of claim 1 wherein said mounting frame further comprises as column rack for holding a chromatographic column.

17. The system of claim 1 wherein said software comprises a software suite that includes a library of one or more flow scheme phases selected from the group consisting of equilibration, sample application, column activation, column washing, elution, column preparation, and tests of column performance, and said software is further programmable for user creation of a flow scheme by selecting and assembling phases from said library.

18. The system of claim 1 wherein said fluid manipulation components include at least one each of valves, pumps, mixers, sample loops, detectors, and fraction collectors.

19. The system of claim 1 wherein said machine-readable data characterizing said fluid manipulation component is data identifying said fluid manipulation component as a member selected from the group consisting of a valve, a pump, a mixer, a sample loop, a detector, and a fraction collector.

20. The system of claim 1 wherein said machine-readable data characterizing said fluid manipulation component includes data representative of operational status of said fluid manipulation component.

21. The system of claim 1 wherein said microcontrollers contain radio-frequency identification tags encoding said data characterizing said fluid manipulation component.

22. The system of claim 21 wherein said radio-frequency identification tags allow updating of said data.

23. The system of claim 1 further comprising a touch screen for user manipulation of said software.

24. The system of claim 1 further comprising a tablet personal computer for user manipulation of said software.

25. The system of claim 1 wherein said software is comprised in a personal computer external to said mounting frame.

26. The system of claim 1 wherein said software is comprised in a personal computer incorporated into said mounting frame.

27. A system for operating a plurality of workstations, each said workstation comprising a plurality of fluid manipulation components joined in a flow scheme for directing fluids to and from a chromatographic separation device and for operating said flow scheme according to a selected protocol, each workstation operating independently of all other said workstations, and each workstation comprising a plurality of modules, a mounting frame, and software in accordance with claim 1, and wherein said software for all said workstations are consolidated in a single computer.

* * * * *